United States Patent
Yoon et al.

(10) Patent No.: US 12,084,798 B2
(45) Date of Patent: Sep. 10, 2024

(54) APPARATUS AND METHOD FOR MANUFACTURING FIBROUS WEB, FIBRILLA FIBER AGGREGATE, OR NONWOVEN FABRIC, AND FIBROUS WEB, FIBRILLA FIBER AGGREGATE, OR NONWOVEN FABRIC MANUFACTURED THEREBY

(71) Applicant: SAMYANG HOLDINGS CORPORATION, Seoul (KR)

(72) Inventors: Hye Sung Yoon, Yongin-si (KR); Jin Su Kim, Yongin-si (KR)

(73) Assignee: SAMYANG HOLDINGS CORPORATION, Seoul (KR)

( * ) Notice: Subject to any disclaimer, the term of this patent is extended or adjusted under 35 U.S.C. 154(b) by 293 days.

(21) Appl. No.: 17/613,560

(22) PCT Filed: Jun. 12, 2019

(86) PCT No.: PCT/KR2019/007068
§ 371 (c)(1),
(2) Date: Nov. 23, 2021

(87) PCT Pub. No.: WO2020/241960
PCT Pub. Date: Dec. 3, 2020

(65) Prior Publication Data
US 2022/0243373 A1    Aug. 4, 2022

(30) Foreign Application Priority Data

May 24, 2019    (KR) .................. 10-2019-0061369

(51) Int. Cl.
*D04H 17/12*    (2006.01)
*A61L 24/08*    (2006.01)
(Continued)

(52) U.S. Cl.
CPC .............. *D04H 17/12* (2013.01); *A61L 24/08* (2013.01); *A61L 31/042* (2013.01); *D04H 1/44* (2013.01); *D04H 1/70* (2013.01); *D10B 2509/022* (2013.01)

(58) Field of Classification Search
CPC .............. D04H 17/12; D04H 1/44; D04H 1/70
(Continued)

(56) References Cited

U.S. PATENT DOCUMENTS

| | | | |
|---|---|---|---|
| 5,473,795 A | 12/1995 | Spix et al. |
| 6,037,282 A | 3/2000 | Milding et al. |

(Continued)

FOREIGN PATENT DOCUMENTS

| | | | |
|---|---|---|---|
| GB | 1287311 A | * 8/1972 | .............. B21F 45/10 |
| GB | 2 096 192 A | 10/1982 | |

(Continued)

OTHER PUBLICATIONS

Machine_English_translation_KR_20180064283_A; Kim et al; Method for preparing fibrous web fibrillar fiber or nonwoven fabric and fibrous web fibrillar fiber or nonwoven fabric prepared thereby; Jun. 14, 2018; EPO; whole document (Year: 2023).*

(Continued)

*Primary Examiner* — Tahseen Khan
(74) *Attorney, Agent, or Firm* — Birch, Stewart, Kolasch & Birch, LLP

(57) ABSTRACT

The present invention relates to an apparatus for manufacturing a fibrous web, a fibrilla fiber aggregate, or a nonwoven fabric by using a woven fabric, a method for manufacturing a fibrous web, a fibrilla fiber aggregate, or a nonwoven fabric by using the apparatus, and a fibrous web, a fibrilla fiber aggregate, or a nonwoven fabric manufactured by the method, especially, a fibrous web, a fibrilla fiber aggregate, or a nonwoven fabric for use in a hemostatic agent or an anti-adhesive agent.

20 Claims, 1 Drawing Sheet

(51) Int. Cl.
    *A61L 31/04*     (2006.01)
    *D04H 1/44*     (2006.01)
    *D04H 1/70*     (2012.01)

(58) Field of Classification Search
    USPC ..................................................... 428/219
    See application file for complete search history.

(56) References Cited

U.S. PATENT DOCUMENTS

| | | |
|---|---|---|
| 2012/0115384 A1 | 5/2012 | Fitz et al. |
| 2013/0273283 A1* | 10/2013 | Feng ................ C09K 21/14 428/401 |
| 2018/0036414 A1 | 2/2018 | Kim et al. |

FOREIGN PATENT DOCUMENTS

| | | | |
|---|---|---|---|
| JP | 55-103314 A | 8/1980 | |
| JP | 10-504613 A | 5/1998 | |
| KR | 10-0254149 B1 | 5/2000 | |
| KR | 10-2009-0014273 A | 2/2009 | |
| KR | 10-2013-0101109 A | 9/2013 | |
| KR | 10-1588433 B1 | 2/2016 | |
| KR | 10-2016-0123422 A | 10/2016 | |
| KR | 10-2018-0064283 A | 6/2018 | |
| KR | 2018064283 A * | 6/2018 | ............. D01G 15/00 |

OTHER PUBLICATIONS

International Search Report (PCT/ISA/210) issued in PCT/KR2019/007068, dated Feb. 21, 2020.

\* cited by examiner

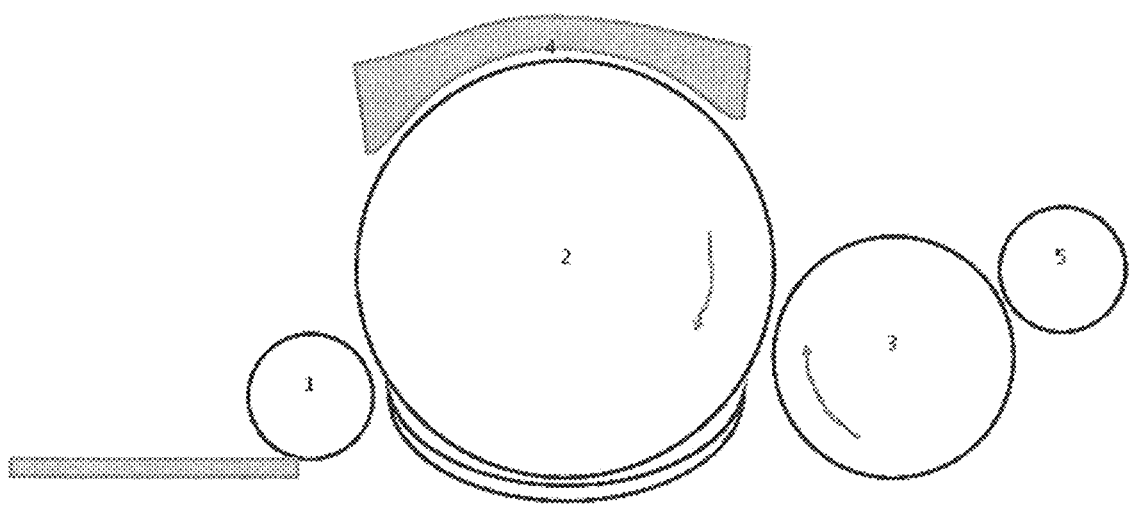

APPARATUS AND METHOD FOR MANUFACTURING FIBROUS WEB, FIBRILLA FIBER AGGREGATE, OR NONWOVEN FABRIC, AND FIBROUS WEB, FIBRILLA FIBER AGGREGATE, OR NONWOVEN FABRIC MANUFACTURED THEREBY

TECHNICAL FIELD

The present invention relates to a machine for preparing fibrous web, fibrillar fiber aggregate or nonwoven fabric by using woven fabric, a method for preparing fibrous web, fibrillar fiber aggregate or nonwoven fabric by using the machine, and fibrous web, fibrillar fiber aggregate or nonwoven fabric prepared by the method, in particular, fibrous web, fibrillar fiber aggregate or nonwoven fabric for hemostatic or antiadhesive use.

BACKGROUND ART

Nonwoven fabric refers to a fabric product prepared by entangling various fibers according to their interacting properties to form a web in a sheet (cloth) form and combining them by mechanical and physical means, without passing through processes of twining, weaving, knitting, etc.

A method for preparing nonwoven fabric generally consists of three (3) procedures of web formation→web combination→processing, etc. The web formation is a procedure of making a web by dispersing and stacking fibers on a conveyer with a thickness as uniform as possible. The web combination is a procedure of entangling or bonding fiber aggregate by giving suitable strength to provide shape stability, in order not to let the fibers separated. The processing is a procedure of completing nonwoven fabric through dyeing or other process necessary for the final use.

Nonwoven fabric preparation is divided into wet method and dry method according to the manner of web formation. The wet method and the dry method are distinguished according to whether the web is formed in a wet condition or in a dry condition. That is, in the dry method, web is formed from fibers in air, whereas in the wet method, fibers are dispersed in liquid to obtain web. As such, web formation methods are sorted according to the medium in which the fibers are dispersed, i.e., air or liquid. Or, nonwoven fabric may also be divided into long fiber nonwoven fabric and short fiber nonwoven fabric according to the kind of fiber.

Oxidized regenerated cellulose (ORC) is a known absorptive hemostatic material. There are many disclosed methods for forming various types of hemostatic products based on oxidized cellulose (OC) in powder, woven fabric, nonwoven fabric, knitted fabric, or other form or combination thereof. The presently used hemostatic dressing for affected part comprises knitted or nonwoven fabric comprising oxidized regenerated cellulose (ORC).

Korean Patent Laid-open Publication No. 2013-0101109 discloses a method of manufacturing a resorbable hemostatic nonwoven dressing, comprising the steps of a) providing cellulose yarn having filaments of minimal twist; b) forming a multi-yarn, single feed circular knitted cellulose fabric having minimal twist; c) scouring the cellulose fabric; d) oxidizing the scoured fabric; e) pliabilizing the oxidized fabric; f) de-knitting the pliabilized fabric to form a continuous strand having a crimp from about 2.0 crimps/cm (5 crimps/inch) to about 4.7 crimps/cm (12 crimps/inch); g) cutting the continuous strand to form staples, said staples having length from about 3.8 to about 10.8 cm (about 1½ to about 4¼ inches); h) carding the staples into a carded batt; i) needle-punching and three-dimensionally entangling the carded batt to form a single layer non-woven felt.

However, the above method has a problem that the manufacturing process is long and complicated because it comprises the steps of pliabilizing the oxidized fabric, de-knitting the pliabilized fabric to form a continuous strand, and cutting the continuous strand to form staple fibers in a specific length.

In addition, most of machines generally used for manufacturing fibrous web, nonwoven fabric or the like use, as raw materials tufts of fibers scrapped into short fibers already, and a method for manufacturing fibrous web, nonwoven fabric, etc. in a short time by feeding the fabric directly and conducting the cutting and combing simultaneously has not been known yet.

In particular, according to the characteristics of the machine for manufacturing fibrous web, nonwoven fabric, etc., the physical properties of the formed fibrous web and nonwoven fabric change sensitively. The physical properties of the formed fibrous web and nonwoven fabric are determined even by slight difference in operation speed of each component, as well as by the order of combining the components, existence or absence of tooth in each component of the machine, physical features of the tooth such as shape, length, angle, arrangement, etc. Thus, it is needed to develop a machine capable of manufacturing good fibrous web and nonwoven fabric with optimized combination of components and operating condition, and a fibrous web and nonwoven fabric manufactured by using the machine and having good hemostatic or antiadhesive effect.

CONTENTS OF THE INVENTION

Problems to be Solved

The purpose of the present invention is to provide a machine capable of preparing fibrous web, fibrillar fiber aggregate or nonwoven fabric from woven fabric in a simple process.

Another purpose of the present invention is to provide a method for preparing fibrous web, fibrillar fiber aggregate or nonwoven fabric by using the machine.

Still another purpose of the present invention is to provide fibrous web, fibrillar fiber aggregate or nonwoven fabric which is prepared by the method and can be used particularly for hemostatic or antiadhesive use.

Technical Means

An aspect of the present invention provides a machine for preparing fibrous web, fibrillar fiber aggregate or nonwoven fabric from woven fabric, the machine comprising a feed roller; a cylinder equipped with a flat bar on a surface thereof; a doffer; and a stripper; wherein teeth are formed on the surface of each of the feed roller, flat bar, cylinder, doffer and stripper, and wherein the machine is operated so that the woven fabric is fed via the feed roller into the cylinder, passes between the flat bar and the cylinder, and then passes through the doffer and the stripper sequentially.

Another aspect of the present invention provides a method for preparing fibrous web, the method comprising a step of passing woven fabric through the above machine of the present invention to process into fibrous web.

Still another aspect of the present invention provides a method for preparing fibrillar fiber aggregate, the method comprising the steps of: passing woven fabric through the above machine of the present invention to process into fibrous web; and calendaring a plurality of the fibrous webs.

Still another aspect of the present invention provides a method for preparing nonwoven fabric, the method comprising the steps of: passing woven fabric through the above machine of the present invention to process into fibrous web; combining a plurality of the fibrous webs in a non-weaving manner; and calendaring the combined plurality of the fibrous webs.

Still another aspect of the present invention provides fibrous web which is prepared by the above method for preparing fibrous web of the present invention and has a density of from 10 g/m² to 60 g/m².

Still another aspect of the present invention provides fibrillar fiber aggregate which is prepared by the above method for preparing fibrillar fiber aggregate of the present invention and has a density of from 100 g/m² to 600 g/m².

Still another aspect of the present invention provides nonwoven fabric which is prepared by the above method for preparing nonwoven fabric of the present invention and has a density of from 50 g/m² to 600 g/m².

Still another aspect of the present invention provides a hemostatic or an antiadhesive comprising the fibrous web of the present invention.

Still another aspect of the present invention provides a hemostatic or an antiadhesive comprising the fibrillar fiber aggregate of the present invention.

Still another aspect of the present invention provides a hemostatic or an antiadhesive comprising the nonwoven fabric of the present invention.

Effect of the Invention

According to the present invention, fibrous web, fibrillar fiber aggregate or nonwoven fabric can be prepared from woven fabric in a simple process, and the fibrous web, fibrillar fiber aggregate or nonwoven fabric prepared as such can be used suitably as a hemostatic or an antiadhesive particularly.

BRIEF EXPLANATION OF THE DRAWINGS

FIG. 1 schematically shows an embodiment of a machine for preparing fibrous web, fibrillar fiber aggregate or nonwoven fabric of the present invention (teeth formed on the surface of the feed roller, flat bar, cylinder, doffer and stripper are not shown).

CONCRETE MODE FOR CARRYING OUT THE INVENTION

The present invention is explained in detail below.

As used herein, the term "fabric" is a concept including knit.

In a preferable embodiment, the tensile strength of the fabric may be, for example, from 4 kgf to 20 kgf (more concretely, from 5 kgf to 18 kgf, and even more concretely, from 6 kgf to 15 kgf). If the tensile strength of the fabric is lower than the above level, it may not be cut efficiently and may be in powdery shape, and to the contrary, if the tensile strength of the fabric is higher than the above level, the cutting may not be complete and thus there may be unarranged parts in the product.

In an embodiment, the density of the fabric that can be used in the present invention may be, for example, from 30 g/m² to 150 g/m² (more concretely, from 40 g/m² to 120 g/m², and even more concretely, from 50 g/m² to 100 g/m²). If the density of the fabric is higher than the above level, it may not be processed into fibrous web easily, and to the contrary, if the density of the fabric is lower than the above level, the amount of fiber in the machine becomes too small and thus the prepared fibrous web may be torn or have weak properties and the productivity may decrease.

In an embodiment, the fabric may be oxidized regenerated cellulose (ORC), oxidized cellulose (OC) or a combination thereof.

In the present invention, the oxidized (regenerated) cellulose means oxidized (regenerated) cellulose having carboxylic acid group (—COOH). In an embodiment, the amount of carboxylic acid group (i.e., degree of oxidation) may be from 13% by weight to 24% by weight.

According to an embodiment of the present invention, in order to strengthen the antiadhesive effect of the prepared fibrous web, fibrillar fiber aggregate or nonwoven fabric, oxidized (regenerated) cellulose having a degree of oxidation of from 13% by weight to 17% by weight may be used.

According to another embodiment of the present invention, in order to strengthen the hemostatic effect of the prepared fibrous web, fibrillar fiber aggregate or nonwoven fabric, oxidized (regenerated) cellulose having a degree of oxidation of from greater than 17% by weight to 24% by weight (for example, from 18% by weight to 24% by weight) may be used.

Oxidized (regenerated) cellulose may be prepared according to a known method in this field of art, for example, according to a method disclosed in U.S. Pat. Nos. 7,279,177, 7,645,874, etc. but it is not especially limited thereto.

The machine for preparing fibrous web, fibrillar fiber aggregate or nonwoven fabric of the present invention conducts the work of carding woven fabric.

As used herein, the term "carding" or "carding process" has a meaning encompassing a procedure of cutting and combing (also may be referred to as "brushing") the fibers constituting the woven fabric to form fibrous web.

The machine of the present invention for conducting such a carding process comprises a feed roller; a cylinder equipped with a flat bar on a surface thereof; a doffer; and a stripper; wherein teeth are formed on the surface of each of the feed roller, flat bar, cylinder, doffer and stripper, and wherein the machine is operated so that the woven fabric is fed via the feed roller into the cylinder, passes between the flat bar and the cylinder, and then passes through the doffer and the stripper sequentially.

The feed roller plays a role of feeding the woven fabric into the cylinder. In an embodiment, the machine of the present invention may comprise one or more (for example, one to three) such feed rollers.

The woven fabric fed via the feed roller into the cylinder is subjected to cutting and combing during its passage between the flat bar and the cylinder. Concretely, the woven fabric is fed between the cylinder wrapped with a metallic wire having teeth formed thereon and the teeth of the flat bar equipped on the cylinder, and cut and scraped in short fiber form and combed simultaneously, between the two kinds of the teeth with different features from each other.

In an embodiment, the machine of the present invention may comprise one or more (for example, one to two) cylinders equipped with such flat bar. Also, in an embodiment of the machine of the present invention, one or more (for example, two to ten, three to eight, or three to four) flat bars per cylinder may be equipped.

The doffer plays a role of detaching the scraped woven fabric distributed on the surface of the cylinder and finally combing it to form fibrous web. In an embodiment, the machine of the present invention may comprise one or more (for example, one to two) such doffers.

The stripper plays a role of moving the fibrous web formed through the doffer from one roller to other roller. In an embodiment, the machine of the present invention may comprise one or more (for example, one to three) such strippers.

In an embodiment, as well as the above-explained constitutional elements, the machine of the present invention may further comprise one or more additional constitutional elements, for example, a take-in roller and/or an additional roller to move the prepared fibrous web.

In the machine of the present invention, teeth are formed on the surface of each of the feed roller, flat bar, cylinder, doffer and stripper.

The teeth play a role of penetrating into the woven fabric, disentangling inside of the woven fabric, and mixing the fibers constituting the woven fabric, and their heights, angles, thicknesses, numbers, etc. may be selected properly for respective components within scopes capable of achieving the purpose of the present invention.

In an embodiment, the teeth formed on the surface of the feed roller may satisfy one or more conditions of a height of from 2.0 to 6.0 mm (more concretely, from 3.0 to 5.0 mm, or from 3.2 to 5.0 mm), an angle of from 50 to 85° (more concretely, from 55 to 80°, from 60 to 85°, or from 65 to 80°), a thickness of from 0.5 to 2.5 mm (more concretely, from 1.0 to 2.0 mm, or from 1.0 to 1.8 mm), a number of from 3 to 20/inch (more concretely, from 4 to 18/inch, or from 5 to 15/inch), and preferably satisfy all of the above.

In an embodiment, the teeth formed on the surface of the cylinder may satisfy one or more conditions of a height of from 2.0 to 6.0 mm (more concretely, from 3.0 to 5.0 mm, or from 2.0 to 4.0 mm), an angle of from 50 to 85° (more concretely, from 55 to 80°, from 60 to 85°, or from 65 to 80°), a thickness of from 0.5 to 2.5 mm (more concretely, from 0.5 to 1.5 mm, or from 0.5 to 1.2 mm), a number of from 3 to 20/inch (more concretely, from 4 to 18/inch, or from 6 to 12/inch), and preferably satisfy all of the above.

In an embodiment, the teeth formed on the surface of the flat bar may satisfy one or more conditions of a height of from 0.5 to 5.0 mm (more concretely, from 0.5 to 4.5 mm, or from 0.5 to 4.0 mm), an angle of from 50 to 90° (more concretely, from 60 to 90°, or from 70 to 90°), a thickness of from 0.5 to 2.5 mm (more concretely, from 0.5 to 1.5 mm, or from 0.8 to 1.2 mm), a number of from 3 to 20/inch (more concretely, from 4 to 15/inch, or from 4 to 10/inch), and preferably satisfy all of the above.

In an embodiment, the teeth formed on the surface of the doffer may satisfy one or more conditions of a height of from 2.0 to 6.0 mm (more concretely, from 2.5 to 5.5 mm, or from 3.0 to 5.0 mm), an angle of from 30 to 80° (more concretely, from 35 to 70°, or from 40 to 65°), a thickness of from 0.5 to 2.5 mm (more concretely, from 0.5 to 1.5 mm, or from 0.6 to 1.2 mm), a number of from 3 to 20/inch (more concretely, from 5 to 18/inch, or from 8 to 14/inch), and preferably satisfy all of the above.

In an embodiment, the teeth formed on the surface of the stripper may satisfy one or more conditions of a height of from 2.0 to 6.0 mm (more concretely, from 2.5 to 5.5 mm, or from 3.0 to 5.0 mm), an angle of from 30 to 80° (more concretely, from 35 to 70°, or from 35 to 55°), a thickness of from 0.5 to 2.5 mm (more concretely, from 0.5 to 1.5 mm, or from 0.8 to 1.5 mm), a number of from 3 to 20/inch (more concretely, from 5 to 18/inch, or from 8 to 14/inch), and preferably satisfy all of the above.

In preparing fibrous web by using the machine of the present invention, the interactions of the feed roller speed, cylinder speed and doffer speed affect the physical properties of the prepared fibrous web.

The woven fabric is conveyed via the feed roller to the cylinder, and the woven fabric passing through the cylinder and the flat bar is scrapped in short fiber form and combed, and then arrives at the action area of the doffer. Since the speed of the doffer surface is relatively lower than of the cylinder surface (conventionally $1/30$ or less), all the woven fabric coming out through the cylinder and the flat bar is scrapped in short fiber form and combed, and then finally combed between the cylinder and the doffer. The unscrapped woven fabric returns to the cylinder, and the woven fabric in the doffer is combed to be a state for easy separation as web. That is, the thin layer in the cylinder becomes a thick layer in the doffer, and it can be condensed to prepare a thick fibrous web.

In an embodiment, if the speed of the cylinder is high, the action of scrapping and combing due to the teeth of the cylinder and the flat bar is good and the carding is done more effectively while the efficiency of doffing action is low. In addition, the fibrous layer gathering in the doffer may become thick or thin according to increasing or decreasing the speed of the doffer. As a result, the time for the woven fabric scrapped in the doffer to receive the combing action of the cylinder increases or decreases. If the speed of the doffer is too high, the combing time becomes short and the quality of the web becomes poor, and to the contrary, if the speed of the doffer is too low, the doffing efficiency becomes low.

In an embodiment, in preparing fibrous web by using the machine of the present invention, the feed roller speed may be from 0.1 to 1 mpm (meter per minute), more concretely from 0.2 to 0.8 mpm, and even more concretely from 0.3 to 0.7 mpm.

In an embodiment, in preparing fibrous web by using the machine of the present invention, the cylinder speed may be from 100 to 350 rpm (revolution per minute), more concretely from 150 to 300 rpm, and even more concretely from 170 to 230 rpm.

In an embodiment, in preparing fibrous web by using the machine of the present invention, the doffer speed may be from 2 to 4 mpm (meter per minute), more concretely from 2.5 to 4 mpm, and even more concretely from 2.8 to 3.8 mpm.

In an embodiment, in preparing fibrous web by using the machine of the present invention, preferably two or more of the feed roller speed, cylinder speed and doffer speed, and more preferably all of them can be within each of the above-stated ranges.

A method for preparing fibrous web according to the present invention comprises a step of passing woven fabric through the above machine of the present invention to process into fibrous web. That is, in the method for preparing fibrous web of the present invention, the woven fabric is subjected to cutting and combing, and is processed (i.e., carding) in a form of fibrous web in the machine.

In an embodiment, the method for preparing fibrous web of the present invention may further comprise a step of stacking the fibrous webs after the processing step into a batt. In this stacking step, a plurality (for example, from 5 to 15, from 5 to 14, from 5 to 13, from 5 to 12, or from 5 to 11) of the fibrous webs can be stacked to form a fibrous web batt.

In an embodiment, the fibrous web prepared according to the method of the present invention has a density of preferably from 10 g/m² to 60 g/m², and more preferably from 15 g/m² to 30 g/m². If the density of the fibrous web is lower than the above level, the cohesion on the web is weak and there may be a problem that the constant shape cannot be maintained. To the contrary, if the density of the fibrous web is higher than the above level, it becomes too bulky and there may be a problem that web separation may occur in web stacking.

A method for preparing fibrillar fiber aggregate according to the present invention comprises a step of calendaring a plurality of the fibrous webs prepared as above.

There is no special limitation to the device and operation condition for the calendaring step, and proper ones can be selected from known devices and operation conditions within scopes capable of achieving the purpose of the present invention.

In an embodiment, the fibrillar fiber aggregate prepared according to the method of the present invention has a density of preferably from 100 g/m² to 600 g/m², and more preferably from 150 g/m² to 300 g/m². If the density of the fibrillar fiber aggregate is lower than the above level, the hemostatic effect may be insufficient, and to the contrary, if the density of the fibrillar fiber aggregate is higher than the above level, the cohesion may decrease and thus web separation may occur in use.

A method for preparing nonwoven fabric according to the present invention comprises the steps of: combining a plurality of the fibrous webs prepared as above in a non-weaving manner; and calendaring the combined plurality of the fibrous webs.

As the method of combining fibrous webs in a non-weaving manner, a method known in this field of art, for example, needle punching method, thermal bonding method, melt blow method, spunlace method, stretch bond method, etc. may be used, but it is not especially limited thereto. In an embodiment, a plurality of the fibrous webs are combined by needle punching, wherein a plurality of the fibrous webs (or fibrous web batt) is fed to a needle punching process and when it passes through the needle punching device, a bed of barbed needles penetrates it and the barbed needles entangle the fibers three-dimensionally and increase the structural density.

The plurality of the fibrous webs combined in a non-weaving manner as such is then subjected to a calendaring step. There is no special limitation to the device and operation condition for the calendaring step, and proper ones can be selected from known devices and operation conditions within scopes capable of achieving the purpose of the present invention.

In an embodiment, the nonwoven fabric prepared according to the method of the present invention has a density of preferably from 50 g/m² to 600 g/m², and more preferably from 80 g/m² to 300 g/m². If the density of the nonwoven fabric is lower than the above level, the hemostatic effect may be insufficient, and to the contrary, if the density of the nonwoven fabric is higher than the above level, the cohesion may decrease and thus web separation may occur in use.

The fibrous web, fibrillar fiber aggregate and/or nonwoven fabric prepared according to the present invention can be used suitably as a hemostatic or an antiadhesive, and in particular, used suitably as a hemostatic.

Therefore, according to another aspect of the present invention, a hemostatic or an antiadhesive comprising the fibrous web, fibrillar fiber aggregate or nonwoven fabric according to the present invention is provided.

The present invention will be explained below in more detail with reference to the following Examples. However, the Examples are only to illustrate the invention, and the scope of the present invention is not limited thereby in any manner.

EXAMPLES

Example 1

Woven regenerated cellulose with a tensile strength of 10 kgf was oxidized with nitrogen dioxide (degree of oxidation: 19%) and dried. Then, the woven oxidized regenerated cellulose (ORC) was fed into the machine of the present invention and processed into fibrous web in sheet form. The feed roller speed, cylinder speed and doffer speed conditions during the processing are those shown in Table 1 below, and the teeth in the machine satisfied the standard shown in Table 2 below. The density of the one-layered fibrous web as prepared was measured as about 15 g/m². Then, the fibrillar fiber aggregate was formed from the fibrous web prepared above through a calendaring process under the conditions shown in Table 3 below.

TABLE 1

| Feed roller speed (mpm) | Cylinder speed (rpm) | Doffer speed (mpm) |
| --- | --- | --- |
| 0.5 ± 0.2 | 200 ± 30 | 3.0 ± 0.3 |

TABLE 2

| Teeth specification | Feed roller | Cylinder | Flat bar | Doffer | Stripper |
| --- | --- | --- | --- | --- | --- |
| Height (mm) | 3.2 to 5.0 | 2.0 to 4.0 | 0.5 to 3.0 | 3.0 to 5.0 | 3.0 to 5.0 |
| Angle (°) | 60 to 85 | 60 to 85 | 70 to 90 | 40 to 65 | 35 to 55 |
| Thickness (mm) | 1.0 to 1.8 | 0.5 to 1.2 | 0.8 to 1.2 | 0.6 to 1.2 | 0.8 to 1.5 |
| Number (per inch) | 5 to 15 | 6 to 12 | 4 to 10 | 8 to 14 | 8 to 14 |

TABLE 3

| Spring elongation (mm) | Roller (rpm) |
| --- | --- |
| 7 | 1.8 |

Example 2

The woven oxidized regenerated cellulose (ORC) obtained in Example 1 was fed into the machine used in Example 1 and processed into fibrous web in sheet form. The feed roller speed, cylinder speed and doffer speed conditions during the processing are those shown in Table 4 below. Then, the prepared plural fibrous webs were combined through needle punching. The needle punching conditions are those shown in Table 5 below. Then, the nonwoven fabric was formed through a calendaring process under the conditions shown in Table 3 above. The density of the nonwoven fabric as prepared was measured as about 85 g/m².

TABLE 4

| Feed roller speed (mpm) | Cylinder speed (rpm) | Doffer speed (mpm) |
| --- | --- | --- |
| 0.5 ± 0.2 | 200 ± 30 | 3.0 ± 0.3 |

TABLE 5

| Inlet (rpm) | Stroke (rpm) | Outlet (rpm) | Distance (mm) | Needle Depth (mm) |
|---|---|---|---|---|
| 0.6 ± 0.1 | 110 ± 30 | 0.7 ± 0.1 | 13 ± 3 | 2.0 ± 0.2 |

Example 3

In order to evaluate the hemostatic effect of the fibrillar fiber aggregate prepared in Example 1, a model small animal test was conducted with nephrectomized rats. As the result, the amount of blood lost until stop bleeding (mean blood loss) was as shown in Table 6 below. In Table 6, Control is the case of natural hemostasis by leaving the rats unattended after partial nephrectomy, and Sample 1 is the case of hemostasis by attaching the fibrillar fiber aggregate after nephrectomy.

TABLE 6

|  | Control (n = 10) | Sample 1 (n = 10) |
|---|---|---|
| Body Weight (g) | 331.9 ± 8.7 | 330.6 ± 5.8 |
| Excised kidney (g) | 0.11 ± 0.01 | 0.113 ± 0.007 |
| Mean blood loss (g) | 2.99 ± 0.78 | 0.90 ± 0.28 |

As can be seen from the result of Table 6, the fibrillar fiber aggregate according to the present invention shows excellent hemostatic effect.

Example 4

In order to evaluate the hemostatic effect of the nonwoven fabric prepared in Example 2, a model small animal test was conducted with nephrectomized rats. As the result, the amount of blood lost until stop bleeding (mean blood loss) was as shown in Table 7 below. In Table 7, Control is the case of natural hemostasis by leaving the rats unattended after partial nephrectomy, and Sample 1 is the case of hemostasis by attaching the nonwoven fabric after nephrectomy.

TABLE 7

|  | Control (n = 10) | Sample 2 (n = 10) |
|---|---|---|
| Body Weight (g) | 332.6 ± 8.96 | 333.5 ± 8.15 |
| Excised kidney (g) | 0.133 ± 0.014 | 0.139 ± 0.02 |
| Mean blood loss (g) | 3.54 ± 0.74 | 1.46 ± 0.61 |

As can be seen from the result of Table 7, the nonwoven fabric according to the present invention shows excellent hemostatic effect.

Comparative Example 1

Woven regenerated cellulose with a tensile strength of 4 kgf was oxidized with nitrogen dioxide (degree of oxidation: 19%) and dried. Then, the woven oxidized regenerated cellulose (ORC) was fed into the machine used in Example 1 and processed into fibrous web in sheet form. The feed roller speed, cylinder speed and doffer speed conditions during the processing are those shown in Table 1 above. Then, the fibrillar fiber aggregate was formed from the fibrous web prepared above through a calendaring process under the conditions shown in Table 3 above.

In order to evaluate the hemostatic effect of the fibrillar fiber aggregate prepared above, a model small animal test was conducted in the same manner as Example 3. As the result, the amount of blood lost until stop bleeding (mean blood loss) was as shown in Table 8 below.

TABLE 8

|  | Control (n = 10) | Comparative Example 1 (n = 10) |
|---|---|---|
| Body Weight (g) | 330.19 ± 8.7 | 303.4 ± 4.9 |
| Excised kidney (g) | 0.11 ± 0.01 | 0.11 ± 0.020 |
| Mean blood loss (g) | 2.99 ± 0.78 | 1.4 ± 0.54 |

As can be seen from the results of Tables 6 and 8, the fibrillar fiber aggregate of Example 1 prepared from woven fabric with a tensile strength of 10 kgf showed remarkably better hemostatic effect than the fibrillar fiber aggregate of Comparative Example 1 prepared from woven fabric with a tensile strength of 4 kgf.

Comparative Example 2

Preparation of fibrillar fiber aggregate was tried by using regenerated cellulose with a tensile strength of 21 kgf in the same manner as Comparative Example 1, but it was impossible to prepare since cutting was not facilitated during the processing and thus web was not formed, and unarranged parts were generated.

EXPLANATION OF REFERENCE NUMERAL

1: Feed roller
2: Cylinder
3: Doffer
4: Flat bar
5: Stripper

The invention claimed is:
1. A method for preparing fibrous web, fibrillar fiber aggregate or nonwoven fabric, the method comprising passing woven fabric starting material comprising oxidized regenerated cellulose through a machine to process into fibrous web, the machine comprising a feed roller; a cylinder equipped with a flat bar on a surface thereof; a doffer; and a stripper,
wherein teeth are formed on the surface of each of the feed roller, flat bar, cylinder, doffer and stripper, and
wherein the woven fabric is fed via the feed roller into the cylinder, passes between the flat bar and the cylinder, and then passes through the doffer and the stripper sequentially.
2. The method of claim 1, wherein:
the teeth formed on the surface of the feed roller satisfy one or more conditions of a height of from 2.0 to 6.0 mm, an angle of from 50 to 85°, a thickness of from 0.5 to 2.5 mm, a number of from 3 to 20/inch;
the teeth formed on the surface of the cylinder satisfy one or more conditions of a height of from 2.0 to 6.0 mm, an angle of from 50 to 85°, a thickness of from 0.5 to 2.5 mm, a number of from 3 to 20/inch;
the teeth formed on the surface of the flat bar satisfy one or more conditions of a height of from 0.5 to 5.0 mm, an angle of from 50 to 90°, a thickness of from 0.5 to 2.5 mm, a number of from 3 to 20/inch;
the teeth formed on the surface of the doffer satisfy one or more conditions of a height of from 2.0 to 6.0 mm, an angle of from 30 to 80°, a thickness of from 0.5 to 2.5 mm, a number of from 3 to 20/inch; and the teeth formed on the surface of the stripper satisfy one or more conditions of a height of from 2.0 to 6.0 mm, an angle of from 30 to 80°, a thickness of from 0.5 to 2.5 mm, a number of from 3 to 20/inch.

3. The of claim 1, wherein:

the feed roller is operated at a speed of from 0.1 to 1 mpm (meter per minute);

the cylinder is operated at a speed of from 100 to 350 rpm (revolution per minute); and the doffer is operated at a speed of from 2 to 4 mpm (meter per minute).

4. The method of claim 1, further comprising calendaring a plurality of the prepared fibrous webs to prepare fibrillar fiber aggregate.

5. The method of claim 1, further comprising:

combining a plurality of the prepared fibrous webs in a non-weaving manner; and calendaring the combined plurality of the fibrous webs to prepare nonwoven fabric.

6. The method of claim 1, wherein the prepared fibrous web has a density of from 10 g/m² to 60 g/m².

7. The method of claim 4, wherein the prepared fibrillar filter aggregate has a density of from 100 g/m² to 600 g/m².

8. The method of claim 5, wherein the prepared nonwoven fabric has a density of from 50 g/m² to 600 g/m².

9. The method of claim 2, further comprising calendaring a plurality of the prepared fibrous webs to prepare fibrillar fiber aggregate.

10. The method of claim 3, further comprising calendaring a plurality of the prepared fibrous webs to prepare fibrillar fiber aggregate.

11. The method of claim 2, further comprising:

combining a plurality of the prepared fibrous webs in a non-weaving manner; and calendaring the combined plurality of the fibrous webs to prepare nonwoven fabric.

12. The method of claim 3, further comprising:

combining a plurality of the prepared fibrous webs in a non-weaving manner; and calendaring the combined plurality of the fibrous webs to prepare nonwoven fabric.

13. The method of claim 2, wherein the prepared fibrous web has a density of from 10 g/m² to 60 g/m².

14. The method of claim 3, wherein the prepared fibrous web has a density of from 10 g/m² to 60 g/m².

15. The method of claim 4, wherein the prepared fibrous web has a density of from 10 g/m² to 60 g/m².

16. The method of claim 5, wherein the prepared fibrous web has a density of from 10 g/m² to 60 g/m².

17. The method of claim 9, wherein the prepared fibrillar fiber aggregate has a density of from 100 g/m² to 600 g/m².

18. The method of claim 10, wherein the prepared fibrillar fiber aggregate has a density of from 100 g/m² to 600 g/m².

19. The method of claim 11, wherein the prepared nonwoven fabric has a density of from 50 g/m² to 600 g/m².

20. The method of claim 12, wherein the prepared nonwoven fabric has a density of from 50 g/m² to 600 g/m².

\* \* \* \* \*